United States Patent [19]

Navarrini et al.

[11] Patent Number: 5,103,049
[45] Date of Patent: Apr. 7, 1992

[54] PROCESS FOR PREPARING PERFLUOROALKENYL-SULFONYL FLUORIDES

[75] Inventors: Walter Navarrini, Milan, Italy; Darryl D. DesMarteau, Clemson, S.C.

[73] Assignee: Ausimont S.r.l., Milan, Italy

[21] Appl. No.: 515,087

[22] Filed: Apr. 26, 1990

[30] Foreign Application Priority Data

Apr. 28, 1989 [IT] Italy .................. 20338 A/89

[51] Int. Cl.$^5$ .......................... C07C 309/80
[52] U.S. Cl. ......................................... 562/825
[58] Field of Search ..................... 562/825, 834

[56] References Cited

U.S. PATENT DOCUMENTS 3,041,317 6/1962 Gibbs et al. ................. 562/825
4,834,922 5/1989 Ezzell et al. ................. 562/825

FOREIGN PATENT DOCUMENTS 60-36454 2/1985 Japan ................. 562/825

OTHER PUBLICATIONS

Kirk–Othmer, Encyclopedia of Chemical Technology, vol. 12, pp. 414–417.

Primary Examiner—Alan Siegel
Assistant Examiner—Margaret Argo
Attorney, Agent, or Firm—Stevens, Davis, Miller & Mosher

[57] ABSTRACT

Process for the synthesis of perfluoroalkenyl-sulfonyl fluorides of formula:

$$R_f-CF=CF-SO_2F$$

wherein:

$R_f$ is F or a perfluoroalkyl of from 1 to 9 carbon atoms, consisting in bringing a perfluoroalkyl-(sulfonyl fluoride) monofluoroacetyl-fluride of formula $R_f-CF_2-CF(COF)SO_2F$ into contact with a reactant constituted by a carbonate of a metal belonging to Groups IA, IIA and IIB of the Periodical Table of the Elements at a temperature comprised within the range of from 150° to 400° C., and then recovering the desired product.

The process is run in continuous.

8 Claims, No Drawings

PROCESS FOR PREPARING PERFLUOROALKENYL-SULFONYL FLUORIDES

DESCRIPTION OF THE INVENTION

The present invention relates to a new process for the synthesis of perfluoroalkenyl-sulfonyl fluorides, in particular perfluorovinyl-sulfonyl fluoride.

As it is known, the perfluoroalkenyl-sulfonyl fluorides find a use as monomers in the preparation of fluorinated polymers containing sulfonyl functions useful for several uses.

In U.S. Pat. No. 3,041,317 a synthesis of perfluoroalkenyl-sulfonyl fluorides of formula $$R_f-CF=CF-SO_2F$$

is reported, wherein $R_f$ is F or a perfluoroalkyl radical or an omega-hydroperfluoroalkyl radical.

The above mentioned synthesis uses as the starting products 2-hydroperfluoroalkyl-sulfonyl fluorides of general formula $$R_f-CF_2-CFH-SO_2F,$$

which are dehydrofluorinated in order to yield perfluoroalkenyl-sulfonyl fluorides inside a plant wherein a stream of reactants is flown under reduced pressure on a catalyst constituted by chrome oxide supported on KCl, at temperatures comprised within the range of from 450° to 630° C.

In particular, in case of perfluorovinyl-sulfonyl fluoride, the reaction is carried out at temperatures comprised within the range of from 508° to 517° C., with a conversion of 51% and a yield of 61% relatively to the starting product converted per each single pass.

R. E. Banks in J. Chem. Soc. (C), 1966, reports a synthesis of perfluorovinyl-sulfonyl fluoride in which the same catalyst and the same operating conditions as reported in the above cited U.S. Pat. No. 3,041,317 are used, with the only difference that the catalyst bed is preheated at 510° C. before the experimental synthesis is carried out.

In the paper by R. E. Banks, the general reactivity of the same molecule is also described.

In both of the above mentioned processes, the starting products are 2-hydroperfluoroalkyl-sulfonyl fluorides having the general formula $$R_f-CFH-CF_2-SO_2F$$

which are synthetized by means of the controlled hydrolysis of the relating sultones having the formula

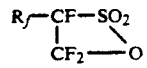

as taught by D. C. England in J. Amer. Chem. Soc. 1960, 82, 6181.

The present Applicants have surprisingly found now that the synthesis of 2-perfluoroalkenyl-sulfonyl fluorides can be carried out in continuously under the atmospheric pressure by using a cheap and easily available reactant and operating at process temperatures which are considerably lower than the temperatures used by the known processes.

Furthermore, when the reactants and the process conditions according to the present invention are used, a simplified synthesis is accomplished, which requires a lower number of intermediate steps. For example, the hydrolysis required in the known processes is no longer necessary in the process according to the present invention.

In particular, according to the present invention, a process for preparing perfluoroalkenyl-sulfonyl fluorides having the general formula (I)

$$R_f-CF=CF-SO_2F \quad (I)$$

wherein:

$R_f$ is selected from among F and a perfluoroalkyl radical of from 1 to 9 carbon atoms, is provided, which consists in bringing a starting product constituted by a perfluoroalkyl-(sulfonyl fluoride) monofluoroacetyl-fluoride having the general formula (II)

$$R_f-CF_2-CF(COF)-SO_2F \quad (II)$$

wherein $R_f$ is as above defined, into contact with a reactant comprising a carbonate of a metal belonging to Groups IA, IIA or IIB of the Periodical Table of the Elements, or mixtures of said carbonates, at a temperature comprised within the range of from 150° to 400° C., and then recovering a compound having the above formula (I) from the effluent of the reaction.

The process according to the present invention is advantageously carried out continuously, preferably under atmospheric pressure, by making a gaseous stream of a perfluoroalkyl-(sulfonyl fluoride) monofluoroacetyl-fluoride used as the starting product (II), flow as a vapour in an inert carrier, preferably nitrogen, on a bed of the reactant constituted by the carbonate placed inside a suitable reactor. For example, as the reactor a glass column or a steel column is used, which preferably contains a bed of the carbonate reactant in a very finely subdivided form. In the reactor also a packing can be used, which is constituted, e.g., by small-size pieces of crushed glass.

The reactant according to the present invention is preferably selected from the group consisting of $Na_2CO_3$, $CaCO_3$, $MgCO_3$, $ZnCO_3$, and mixtures thereof.

The reaction, on which the process according to the present invention is described in the following reaction for exemplifying purposes, relatively to the use of $CaCO_3$ as the carbonate reactant.

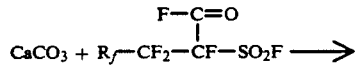

$$\rightarrow R_f-CF=CF-SO_2F + CaF_2 + 2CO_2$$

The amount of reactant used is at least equal to the stoichiometric amount required by the above reaction, but preferably an excess over the stoichiometric amount is used, also according to the degree of crushing of the reactive bed.

The process is carried out under anhydrous conditions, with carrier nitrogen and the reactant bed, as well as the reactor packing, if used, being previously thoroughly deprived of any water, e.g., by means of some hours of heating at about 300° C. Nitrogen is then make flow through a charging trap containing a starting product (II), wherein said nitrogen is saturated with the vapours from said starting product (II), and is then made flow through the reactor maintained at the reaction temperature, at such a flowing rate as to obtain a stay time of the starting product inside the reactor, which is comprised within the range of from 3 to 15 seconds.

The gas stream leaving the reactor is flown through a condenser maintained at a low enough temperature in order to condense all of the reaction products, but not nitrogen, e.g., at a temperature comprised within the range of from −98° C. to −196° C.

The condensed raw reaction product is distilled under reduced pressure and the vapours from the distillation are condensed through a plurality of steps in order to first recover the desired perfluoroalkenyl-sulfonyl fluoride product (I), and then $SO_2$ as a reaction by product. Other byproducts from the process, such as $CO_2$ and $SiF_4$, as well as such decomposition products as, e.g., $CF_3COF$ and $C_2F_4$, are removed by the dynamic vacuum during the distillation.

The conversion of the starting product is generally complete, with yields of the desired product (I), defined as the ratio of the produced mols of product (I) to the reacted mols of starting product (II), being obtained, which are comprised within the range of from 30 to 50%.

The starting products (II) used in the process according to the present invention are synthetized from the corresponding perfluoroalkylene sultones (III):

by means of their isomerization in the presence of catalytic amounts of KF or of trialkylamines, with quantitative yields being obtained, as described by D. C. England in J. Amer. Chem. Soc. 1960, 82, 6181.

The process according to the present invention is particularly useful for the preparation of compounds of formula (I) wherein $R_f$ is either F or a perfluoroalkyl of from 1 to 3 carbon atoms, and preferably for the preparation of trifluorovinyl-sulfonyl fluoride, of perfluoropropenyl-sulfonyl fluoride, or of perfluorobutenyl-sulfonyl fluoride.

In particular, for the synthesis of trifluorovinyl-sulfonyl fluoride

2,3,3,3-tetrafluoro-2-fluorosulfonyl-propionyl fluoride having the formula $CF_3$—$CF(COF)$—$SO_2F$ is used. Said latter compound can be easily synthetized by isomerization of perfluoropropylene sultone

according to the above mentioned method by D. C. England.

The following examples are supplied for merely illustrative purposes, and in no way do they limit the scope of the invention as herein disclosed and claimed.

EXAMPLE 1

In a continuous working plant 1.2 g (5.2 mmol) of

[2.3.3.3-tetrafluoro-2-(fluorosulfonyl)-propionyl fluoride] is charged to a charging trap of "U"-shape.

The charging trap is subsequently connected with the continuous working plant by means of valves.

Previously thoroughly dried nitrogen is flown at a flow rate of 300 cm³/minute through said charging trap, which is kept at the constant temperature of −35° C. throughout the process time.

Nitrogen leaving the charging trap, saturated with the vapours of the starting product, is flown through the reactor maintained at the temperature of 300° C.

During a time of about 1.5 hours, all of the starting product is conveyed through the reactor consisting of a glass column of 1.5 cm of diameter, filled with 40 g of sodium carbonate previously thoroughly dried at 300° C., and packed with 40 g of small pieces of crushed glass.

The reactor leaving gases are flown through two traps kept at the temperature of −196° C., so as to condense all of the reaction products; on the contrary, the nitrogen carrier flows to the discharge stack.

The raw reaction product contained inside both of said collecting traps is distilled under the pressure of $10^{-3}$ torr. The vapours coming from the distillation kettle are made flow through cold traps maintained at temperatures of −80° C. and −110° C.

Inside the trap at −110° C., 0.4 mmol of $SO_2$ condenses; inside the trap at −80° C., 1.6 mmol of trifluorovinyl-sulfonyl fluoride

condenses. $CO_2$, $SiF_4$ and the decomposition products, such as, e.g., $CF_3COF$ and $C_2F_4$ are removed by the dynamic vacuum during the same distillation.

The conversion of the starting product is complete.

The yield, defined as the ratio of the mols of desired product ($CF_2$=$CF$—$SO_2F$) to the reacted mols of the starting product, is of 30%.

EXAMPLE II

According to same modalities as of Example I, using a reactor temperature of 250° C., a flow rate of carrier nitrogen of 400 cm³/minute, and with the temperature of the charging trap being maintained at −10° C., the reaction yield of trifluorovinyl-sulfonyl fluoride, as defined as in Example I, is of 40%.

EXAMPLE III

By following the same modalities as of Example I, but using perfluoro-2-(fluorosulfonyl)-butanoyl fluoride as the starting product, perfluoropropenyl-sulfonyl fluoride is prepared.

EXAMPLE IV

By means of modalities identical to as in Example I, using a reactant bed constituted by $CaCO_3$, the reaction yield of trifluorovinyl-sulfonyl fluoride, as defined as in Example I, is of 18%.

What is claimed is:

1. A process for preparing perfluoroalkenyl-sulfonyl fluorides having the formula (I)

$$R_f-CF=CF-SO_2F \qquad (I)$$

wherein:

$R_f$ is selected from among the group consisting of F and a perfluoroalkyl radical of from 1 to 9 carbon atoms, comprising contacting a perfluoroalkyl-(sulfonyl fluoride) monofluoroacetylfluoride having the formula (II)

$$R_f-CF_2-CF(COF)-SO_2F \qquad (II)$$

wherein $R_f$ has the meaning as defined above, under anhydrous conditions with a reactant selected from the group consisting of carbonates of a metal belonging to Group IA, IIA and IIB of the Periodic Table of the Elements, or mixtures thereof at a temperature within the range of from 150° to 400° C., and then recovering a compound having the above formula (I) from the effluent of the reaction.

2. Process according to claim 1 wherein $R_f$ is fluorine.

3. Process according to claim 1 wherein $R_f$ is selected from the group consisting of perfluoroalkyls containing from 1 to 3 carbon atoms.

4. Process according to claim 1 wherein said temperature is within the range of from 200° to 350° C.

5. Process according to claim 1 wherein said reactant is selected from the group consisting of $Na_2CO_3$, $CaCO_3$, $MgCO_3$, $ZnCO_3$, and mixtures thereof.

6. Process according to claim 1, carried out continuously under atmospheric pressure.

7. Process according to claim 6, wherein the step of contacting said perfluoroalkyl-(sulfonyl fluoride) monofluoroacetylfluoride with said reactant is accomplished by making a gaseous steam, comprising an inert carrier saturated with vapors of said perfluoroalkyl (sulfonyl fluoride) monofluoroacetylfluoride, flow onto a bed of said reactant.

8. Process according to claim 7, wherein said inert carrier is nitrogen.

* * * * *